United States Patent
Sato et al.

(10) Patent No.: US 11,931,200 B2
(45) Date of Patent: Mar. 19, 2024

(54) ULTRASOUND DIAGNOSTIC APPARATUS AND DIAGNOSIS ASSISTING METHOD

(71) Applicant: Hitachi, Ltd., Tokyo (JP)

(72) Inventors: Mika Sato, Tokyo (JP); Yoko Fujihara, Tokyo (JP)

(73) Assignee: FUJIFILM Healthcare Corporation, Chiba (JP)

( * ) Notice: Subject to any disclaimer, the term of this patent is extended or adjusted under 35 U.S.C. 154(b) by 0 days.

(21) Appl. No.: 17/233,849

(22) Filed: Apr. 19, 2021

(65) Prior Publication Data
US 2021/0401396 A1     Dec. 30, 2021

(30) Foreign Application Priority Data
Jun. 25, 2020   (JP) ................... 2020-109604

(51) Int. Cl.
A61B 8/08       (2006.01)
A61B 8/00       (2006.01)
A61B 8/13       (2006.01)

(52) U.S. Cl.
CPC ............ *A61B 8/085* (2013.01); *A61B 8/13* (2013.01); *A61B 8/461* (2013.01)

(58) Field of Classification Search
CPC .......... A61B 8/085; A61B 8/13; A61B 8/461; A61B 8/463; A61B 8/54; A61B 8/4254; A61B 8/488; A61B 8/14; A61B 8/0825; A61B 8/483; G16H 50/20; G16H 30/40; G16H 40/63
See application file for complete search history.

(56) References Cited

U.S. PATENT DOCUMENTS

| | | | | |
|---|---|---|---|---|
| 2006/0004283 | A1* | 1/2006 | Moriyama | G06T 11/00 600/416 |
| 2014/0088427 | A1* | 3/2014 | Tashiro | A61B 8/463 600/443 |
| 2019/0069757 | A1* | 3/2019 | Iwaki | G06T 7/70 |
| 2020/0126223 | A1 | 4/2020 | Kitamura et al. | |

(Continued)

FOREIGN PATENT DOCUMENTS

| | | |
|---|---|---|
| CN | 108348145 A | 7/2018 |
| JP | 2004-159739 A | 6/2004 |
| JP | 2010-172673 A | 8/2010 |

(Continued)

OTHER PUBLICATIONS

Chinese Office Action received in corresponding Chinese Application No. 202110397953.6 dated Jun. 20, 2023.

(Continued)

*Primary Examiner* — Shahdeep Mohammed
*Assistant Examiner* — Fikirte (Fiki) T Ashine
(74) *Attorney, Agent, or Firm* — Mattingly & Malur, PC

(57) ABSTRACT

An image analyzer detects a lesion for each frame (tomographic image). When the lesion is detected, lesion information (detection flag, position information, and size information) is produced. An indication controller causes a mark surrounding the lesion to be displayed when it is judged that a mark display condition is satisfied, based on the lesion information or the like. The indication controller causes the mark to be deleted from a screen when detection of the lesion is continued and a mark display restriction condition is satisfied.

7 Claims, 9 Drawing Sheets

(56) References Cited

U.S. PATENT DOCUMENTS

2020/0160301 A1* 5/2020 Lyman ............... G06T 11/206
2021/0000327 A1* 1/2021 Kitamura ............ H04N 7/183

FOREIGN PATENT DOCUMENTS

| JP | 2020-81742 A | 6/2020 | |
|----|----|----|----|
| WO | 2018/198327 A1 | 11/2018 | |
| WO | 2017/203560 A1 | 3/2019 | |
| WO | WO-2019146066 A1 * | 8/2019 | ........... A61B 1/0005 |

OTHER PUBLICATIONS

Japanese Office Action received in corresponding Japanese Application No. 2020-109604 dated Dec. 5, 2023.
Chinese Office Action received in corresponding Chinese Application No. 202110397953.6 dated Nov. 9, 2023.

* cited by examiner

ULTRASOUND DIAGNOSTIC APPARATUS AND DIAGNOSIS ASSISTING METHOD

CROSS REFERENCE TO RELATED APPLICATION

This application claims priority to Japanese Patent Application No. 2020-109604 filed on Jun. 25, 2020, which is incorporated herein by reference in its entirety including the specification, claims, drawings, and abstract.

TECHNICAL FIELD

The present disclosure relates to an ultrasound diagnostic apparatus and a method of assisting diagnosis, and in particular to a technique of displaying on an ultrasonic image a mark for indicating a lesion.

BACKGROUND

In an ultrasonic examination of a breast, a probe which is brought into contact with a surface of the breast is scanned along the surface of the breast. During the scanning, a real-time tomographic image displayed on a display is observed, and presence or absence of a lesion is judged through the observation. When the lesion is found, the lesion and peripheral tissues thereof are examined in more detail. This is similarly true for an ultrasonic examination of other tissues. In the present disclosure, the lesion refers to a portion which is not healthy or a portion possibly having a disease.

On a tomographic image which changes in real time, it is difficult to visually identify the lesion which temporarily appears on the image. In particular, in the ultrasonic examination of the breast, a tissue which appears on the tomographic image has a multilayer structure, and it is difficult for an inspector to instantaneously identify the lesion included in the tissue.

As a technique for assisting identification of the lesion, there is known CADe (Computer Aided Detection). In this technique, for example, the lesion in the tomographic image is detected for each frame, and the lesion is indicated when the lesion is included in the tomographic image. For example, a mark surrounding the lesion is displayed on the tomographic image. The CADe is used with CAD (Computer Aided Diagnosis), or included in the CAD.

JP 2004-159739 A discloses a medical apparatus having a CAD function. The medical apparatus has a function to automatically select presence or absence of a display of the mark for indicating the lesion. WO 2018/198327 also discloses a medical apparatus having the CAD function. The medical apparatus has a function to display a sub image including a mark for indicating the lesion. Neither of these references discloses a technique which forcibly ends the display of the mark.

In ultrasound diagnostic apparatuses having the CADe function or the CAD function, a mark for indicating the lesion is automatically displayed on the ultrasonic image. The mark typically has a shape surrounding the lesion. Through an appearance of the mark and a continued display of the mark, it is possible to notify the inspector of the presence of a lesion, and the detailed examination of the lesion can thus be promoted. However, if display of the mark is continued beyond a necessary degree after the inspector has recognized the lesion, the mark may become an obstacle in the observation of the ultrasonic image.

When the lesion is identified, the lesion itself is observed in detail, and a connection relationship or the like of the lesion and the peripheral tissues is also observed in detail. During such an observation process, a problem may arise in which a site desired to be observed is covered with the mark. Although the mark may be deleted by manually switching the mark display OFF, such an operation is burdensome to the inspector. In addition, when a line of sight is moved to an operation panel for such an operation, there is a possibility that the lesion may be lost when the line of sight is returned to the ultrasonic image. In particular, in an examination for a group of people (group examination), shortening of an ultrasonic examination period per subject is desired, and minimizing the operation of the inspector and the movement of the line of sight of the inspector is desired.

An advantage of the present disclosure lies in preventing or reducing obstruction of the observation of the ultrasonic image due to a mark when the lesion which is automatically detected is indicated by the mark.

SUMMARY

According to one aspect of the present disclosure, there is provided an ultrasound diagnostic apparatus comprising: an analyzer that detects a lesion included in an ultrasonic image which is a real-time video image, and that outputs lesion information when the lesion is detected; and an indication controller that causes a mark for indicating the lesion to be displayed on the ultrasonic image based on the lesion information, and that restricts display of the mark when a mark display restriction condition is satisfied by a continued detection of the lesion.

According to another aspect of the present disclosure, there is provided a method of assisting diagnosis, the method comprising: detecting a lesion included in an ultrasonic image; displaying a mark which surrounds the lesion on the ultrasonic image based on lesion information which is produced when the lesion is detected; and restricting display of the mark when a mark display restriction condition is satisfied by a continued detection of the lesion.

According to another aspect of the present disclosure, there is provided a program which, when executed, causes the functions of: displaying a mark which surrounds a lesion on an ultrasonic image, based on lesion information which is produced when the lesion included in the ultrasonic image is detected; and restricting display of the mark when a mark display restriction condition is satisfied by a continued detection of the lesion.

BRIEF DESCRIPTION OF DRAWINGS

Embodiment(s) of the present disclosure will be described based on the following figures, wherein.

DESCRIPTION OF EMBODIMENTS

Figure 1:
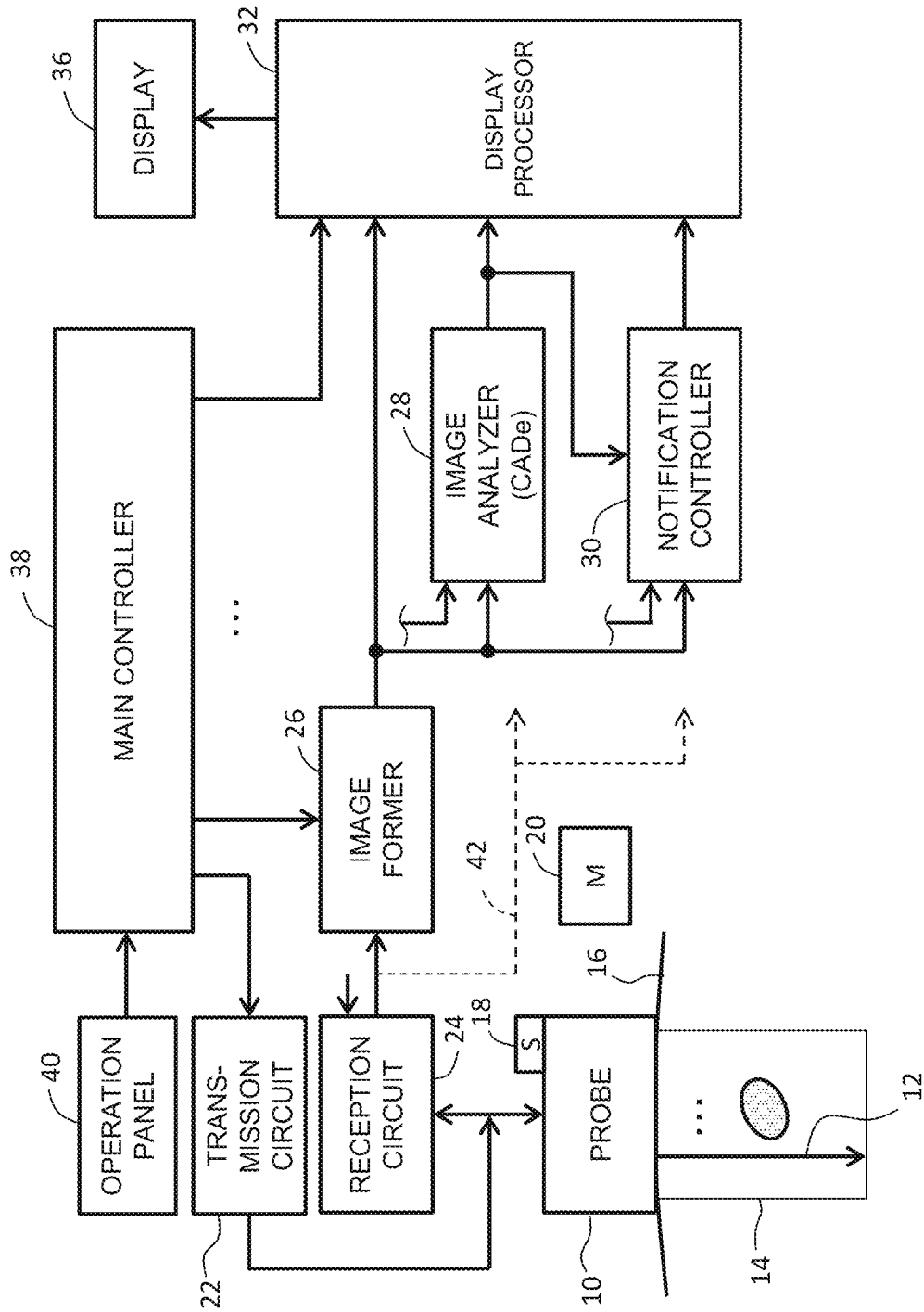
FIG. 1 is a block diagram showing an ultrasound diagnostic apparatus according to an embodiment of the present disclosure.

An embodiment of the present disclosure will now be described with reference to the drawings.

(1) Overview of Embodiment

An ultrasound diagnostic apparatus according to an embodiment of the present disclosure comprises an analyzer, and an indication controller. The analyzer detects a lesion included in an ultrasonic image which is a real-time video image, and outputs lesion information when the lesion is detected. The indication controller causes a mark for indicating the lesion to be displayed on the ultrasonic image based on the lesion information, and restricts display of the mark when a mark display restriction condition is satisfied by a continued detection of the lesion.

According to the above-described structure, in the case in which the lesion is continued to be detected and the mark is continued to be displayed, when a mark display restriction condition is satisfied, the displaying of the mark is restricted. Therefore, obstruction, by the mark, of the observation of the lesion or the peripheral tissues thereof can be prevented or reduced. With a manual restriction of the mark display, a burden is caused in the inspector, but with the above-described structure, no such problem occurs.

In an embodiment, the restriction of the display of the mark is completion of the display of the mark; that is, deletion of the mark. Before the deletion of the mark, the lesion is already identified by the inspector through the displayed mark, and thus, even when the mark is deleted, the lesion is not lost. If necessary, a predetermined operation or a predetermined input may be made to again display the mark. In an embodiment, the mark is a figure surrounding the lesion. Alternatively, the mark display restriction may be maintained for a certain period even after the mark detection is stopped. Alternatively, a display restriction other than the mark deletion (for example, reduction of brightness) may be employed.

In an embodiment, the indication controller judges that the mark display restriction condition is satisfied based on the lesion information. By judging whether or not the mark display condition is satisfied based on the lesion information produced by the detection of the lesion, it becomes possible to improve reliability of the judgment. It may be judged whether or not the mark display restriction condition is satisfied based on a result of an inter-frame correlation calculation, probe measurement position information, or the like.

In an embodiment, the lesion information includes position information which shows a position of the lesion, and size information which shows a size of the lesion. The indication controller judges that the mark display restriction condition is satisfied, based on at least one of the position information or the size information. According to this configuration, judgment of a continued display of the same lesion can be facilitated. In other words, a possibility that a mark will be displayed when a new lesion is detected can be improved.

In an embodiment, the mark display restriction condition includes a time condition which is satisfied when the lesion is continued to be detected over a predetermined period, and a spatial condition which is satisfied when a change of a position of the lesion is within a first range and a change of a size of the lesion is within a second range. By taking into consideration both the time condition and the spatial condition, a state in which detection of the same lesion is continued can be more accurately identified.

In an embodiment, when a freeze operation is performed in a state in which the display of the mark is restricted, the indication controller again displays the mark on the ultrasonic image which is frozen. When the ultrasonic image is stored after the freezing, the mark may be included in the ultrasonic image, so as to facilitate identification of the lesion when the ultrasonic image is observed at a later time. Alternatively, an ultrasonic image with a mark and an ultrasonic image without the mark may be stored together. When a measurement of the lesion is executed after the freezing, the mark may be automatically deleted at a startup of the measurement function.

In an embodiment, the mark has a form which surrounds the lesion. In a state in which the display of the mark is restricted, the indication controller causes another mark, for indicating detection of the lesion, to be displayed at an outer side of the ultrasonic image. According to this configuration, even when the display of the mark is restricted, it is possible to notify the inspector that detection of the lesion is continued, through the display of the other mark. As such another mark, a mark set for identifying a horizontal position and a vertical position of the lesion may be displayed at the outer side of the ultrasonic image. When a plurality of lesions are detected, a plurality of mark sets may be displayed, corresponding to the plurality of lesions.

A method of assisting diagnosis according to an embodiment includes a first step, a second step, and a third step. In the first step, a lesion included in an ultrasonic image is detected. In the second step, a mark which surrounds the lesion is displayed on the ultrasonic image based on lesion information which is produced when the lesion is detected. In the third step, display of the mark is restricted when a mark display restriction condition is satisfied by a continued detection of the lesion.

The method of assisting diagnosis described above is realized by a function of hardware or by a function of software. In the case of the latter, a program for executing the method of assisting diagnosis is installed in an information processor through a transportable recording medium or through a network. The concept of the information processor includes an ultrasound diagnosis apparatus, a computer, and the like. The program for executing the method of assisting diagnosis described above may be non-transitorily stored in a recording medium.

(2) Details of Embodiment

FIG. 1 is a block diagram showing a structure of an ultrasound diagnostic apparatus according to an embodiment of the present disclosure. The ultrasound diagnostic apparatus is a medical apparatus which is placed in a medical institution such as a hospital, and which forms an ultrasonic image based on a reception signal acquired through transmission and reception of ultrasound to and from a living body (subject). In the present embodiment, an organ to be diagnosed by the ultrasound is, for example, a breast.

In a group examination for the breast, it is necessary to identify a lesion in a short time and without overlooking the lesion. The ultrasound diagnostic apparatus according to the present embodiment has the CADe function for automatically detecting the lesion (for example, a tumor image of low brightness) included in the ultrasonic image, in order to assist the identification of the lesion by the inspector. This function will be described later in detail.

A probe 10 functions as a means for transmitting and receiving ultrasound. The probe 10 is a transportable transmission/reception device, and is held and operated by an inspector (a doctor, an inspection technician, or the like). In the ultrasound diagnosis of the breast, a transmission/reception surface of the probe 10 (more specifically, a surface of an acoustic lens) is brought into contact with a surface of a chest of the subject. The probe 10 is manually scanned along the surface of the chest while a tomographic image which is displayed in real time is observed.

In the illustrated example configuration, the probe 10 comprises a transducer array formed from a plurality of transducers which are one-dimensionally arranged. An ultrasound beam (a transmission beam and a reception beam) 12 is formed by the transducer array, and a scanning plane 14 is formed by an electronic scanning of the ultrasonic beam 12. The scanning plane 14 is an observation plane, and is a two-dimensional data capturing region. As a method of electronic scanning of the ultrasound beam 12, there are known an electronic sector scanning method, an electronic linear scanning method, and the like. Alternatively, a convex scanning of the ultrasonic beam 12 may be executed. Alternatively, a 2-D (two-dimensional) transducer array may be provided in the ultrasonic probe 10, and volume data may be acquired from an inside of the living body by a two-dimensional scanning of the ultrasonic beam.

Alternatively, a position measurement device for determining position information of the probe 10 may be provided. The position measurement device is formed from, for example, a magnetic sensor 18 and a magnetic field generator 20. The magnetic sensor 18 is provided on the probe 10 (more accurately, a probe head). A magnetic field generated by the magnetic field generator 20 is detected by the magnetic sensor 18, to thereby acquire three-dimensional coordinate information of the magnetic sensor 18. A position and an orientation of the probe 10 are identified based on the three-dimensional coordinate information.

A transmission circuit 22 functions as a transmission beam former. More specifically, during transmission, the transmission circuit 22 supplies to the transducer array a plurality of transmission signals in parallel to each other. With this process, the transmission beam is formed. During reception, when a reflected wave from within the living body reaches the transducer array, a plurality of reception signals are output in parallel to each other from the plurality of transducers. A reception circuit 24 functions as a reception beam former, and produces beam data by applying a phase alignment and summing process (which is also called a delay and summing process) on the plurality of reception signals.

For each electronic scanning, a plurality of sets of beam data arranged in the electronic scanning direction are formed, which form reception frame data corresponding to the scanning plane 14. Each individual set of beam data is formed from a plurality of sets of echo data arranged in a depth direction. Downstream of the reception circuit 24, a beam data processor is provided, which is not shown in the figures.

An image former 26 is an electronic circuit which produces a tomographic image (B-mode tomographic image) based on the reception frame data. The image former 26 has a DSC (Digital Scan Converter). The DSC has functions such as a coordinate conversion function, a pixel interpolation function, a frame rate conversion function, and the like. More specifically, at the image former 26, a display frame data array is formed based on a reception frame data array. A plurality of sets of display frame data of the display frame data array are a plurality of sets of tomographic image data, and a real-time video image is formed based on these data. Alternatively, an ultrasonic image other than the tomographic image may be produced. For example, a color flow mapping image may be formed, or a three-dimensional image three-dimensionally expressing a tissue may be formed. The display frame data array is sent to a display processor 32 and to an image analyzer 28. As necessary, the display frame data array may be also sent to an indication controller 30.

The image analyzer 28 is a module which realizes the CADe function. The image analyzer 28 executes a lesion detecting process for each frame; that is, for each tomographic image. More specifically, the lesion is detected as a closed region of low brightness through processes such as a binarization process, an edge detection process, and the like, on the tomographic image. When the lesion is detected, lesion information is output from the image analyzer 28. The lesion information includes a lesion detection flag, position information of the lesion, and size information of the lesion.

The position information of the lesion is, for example, information showing a coordinate of a center point (or a point of a center of gravity) of the closed region corresponding to the lesion, or information showing a coordinate of a center point (or a point of a center of gravity) of a figure surrounding the lesion. The size information of the lesion is, for example, information showing a size of the figure surrounding the lesion. For example, a quadrangle circumscribing and surrounding the lesion may be defined, and the size of the lesion may be identified based on a coordinate of the center point of the quadrangle and a coordinate of an upper left corner point of the quadrangle. Under an assumption that the coordinate of the center point is known, the coordinate of the upper left corner point may be regarded as the size information of the lesion. Alternatively, as the size information of the lesion, an area of the closed region corresponding to the lesion may be determined. Alternatively, a plurality of lesions may be detected in parallel to each other.

The indication controller 30 causes a mark for indicating the lesion to be displayed on a screen when a mark display condition is satisfied by a continued detection of the lesion. The indication controller 30 restricts the display of the mark when a mark display restriction condition is satisfied by a further continued detection of the lesion.

More specifically, in the present embodiment, when the lesion is continued to be detected over m frames (where m is an integer greater than or equal to 2) including a current frame, and an amount of movement of the center point between a reference frame and the current frame is within a predetermined range, it is judged that the mark display condition is satisfied, and the mark is displayed. Alternatively, the mark display condition may include a condition related to an amount of change of the size of the lesion. In the present embodiment, an exception condition is employed in which, when a shadow temporarily occurs in the tomographic image and the detection of the lesion is temporarily obstructed by the shadow, it is still regarded that the detection of the lesion is continued. The predetermined range described above may be designated by a user or may be set automatically based on a diagnosis item, an examination target, or the like.

Further, in the present embodiment, when detection of the lesion is continued over n frames (where n is an integer larger than m) including the current frame, the amount of movement of the center point between the reference frame and the current frame is within a first range, and the amount of change of the size between the reference frame and the current frame is within a second range, it is judged that the mark display restriction condition is satisfied. When it is judged that the mark display restriction condition is satisfied, the display of the mark is completed at this point, and the mark disappears from the screen. The first range and the second range may be designated by the user or may be set automatically based on the diagnosis item, the examination target, or the like.

As will be described later, the mark display restriction may be maintained over a certain period from the time when the detection of the lesion is stopped. That is, an extension period may be added to a mark display restriction period, or a mark display restriction period including the extension period may be determined. The extension time may be designated by the user or may be set automatically according to the circumstances. Alternatively, the addition or non-addition of the extension may be selected by the user.

Each of the image former 26, the image analyzer 28, and the indication controller 30 may be formed by a processor. Alternatively, a single processor may function as the image former 26, the image analyzer 28, and the indication controller 30. Alternatively, a CPU to be described later may function as the image former 26, the image analyzer 28, and the indication controller 30.

The display processor 32 has a graphic image production function, a color calculation function, an image combining function, and the like. Outputs of the image former 26, the image analyzer 28, and the indication controller 30 are supplied to the display processor 32. A mark surrounding the lesion is one display element of a graphic image. A display 36 is formed from an LCD, an organic EL display device, or the like. The tomographic image which is a video image is displayed in real time on the display 36, and the mark is displayed as a part of the graphic image. The display processor 32 is formed from, for example, a processor.

A main controller 38 controls operations of the elements shown in FIG. 1. In the present embodiment, the main controller 38 is formed from a CPU and a program. An operation panel 40 is connected to the main controller 38. The operation panel 40 is an input device, and has a plurality of switches, a plurality of buttons, a trackball, a keyboard, or the like.

In the present embodiment, the display frame data array is supplied to the image analyzer 28 and the indication controller 30, but alternatively, the reception frame data array may be supplied to the image analyzer 28 and the indication controller 30 (refer to reference numeral 42).

Figure 2:
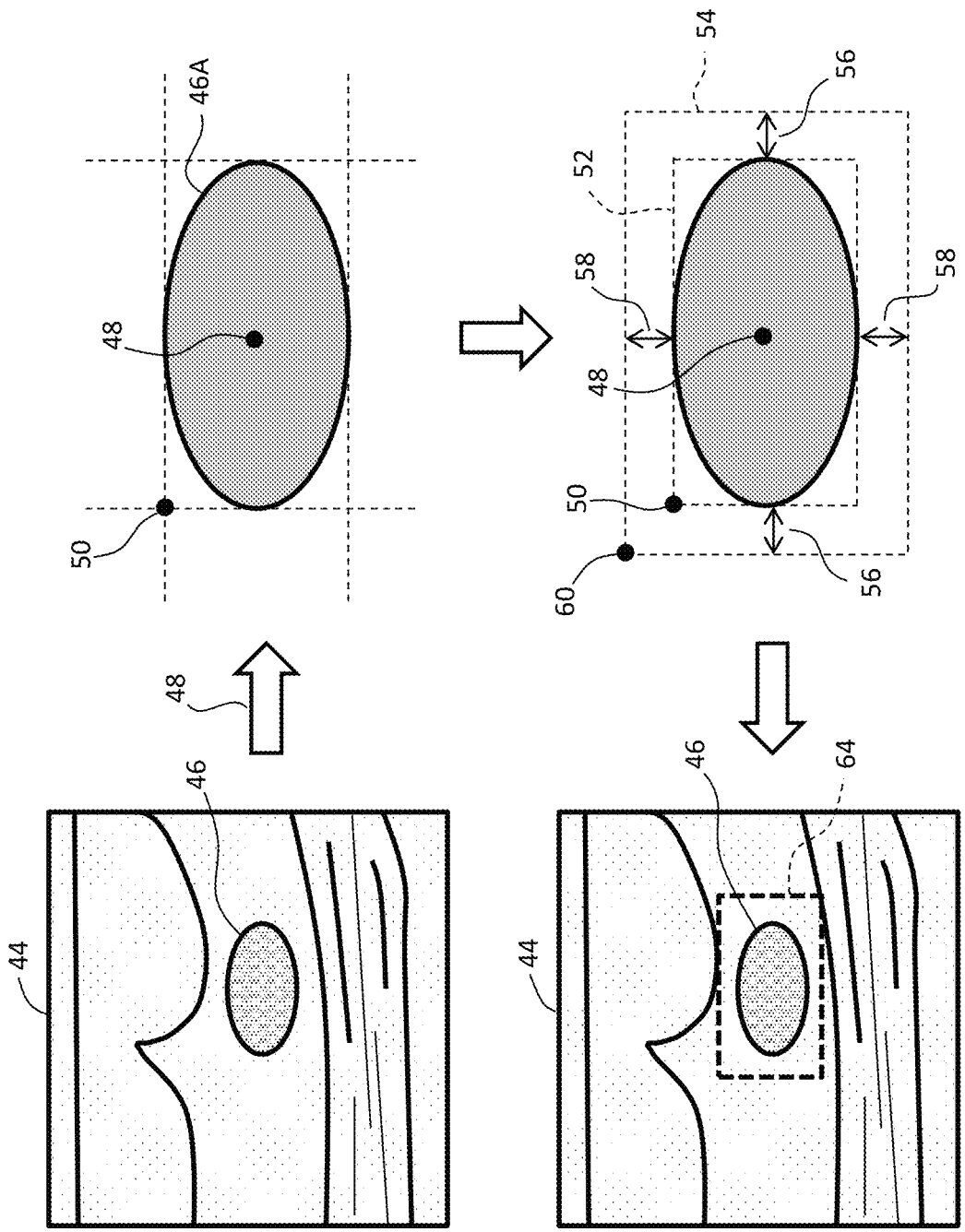
FIG. 2 is a diagram showing a mark displaying process.

FIG. 2 shows a mark display process. A tomographic image 44 includes a lesion 46. Through binarization of the tomographic image 44, a binarized image is produced. Edge detection or region detection is applied to the binarized image, to extract a binarized lesion 46A. A quadrangle 52 which circumscribes the lesion 46A is defined by, for example, coordinates of respective ends of the lesion 46A in the horizontal direction, and coordinates of respective ends of the lesion 46A in the vertical direction. In actual practice, a coordinate of a center point 48 and a coordinate of an upper left corner point 50 are specified.

A quadrangle 54 is defined as a figure at an outer side of the quadrangle 52, with certain margins 56 and 58 in the horizontal direction and the vertical direction. The quadrangle 54 is displayed as a mark 64 on the tomographic image. The mark 64 is a figure that surrounds the lesion 46 and a periphery thereof. In the illustrated example configuration, the mark 64 is formed from a broken line. A display form of the mark 64 may be freely chosen. For example, a mark formed from a solid line may be displayed, or a mark including four elements which show only four corner portions may be displayed. Alternatively, a circular mark or an elliptical mark may be displayed.

In any case, the mark 64 is displayed on the tomographic image 44 when the mark display condition is satisfied. With the display of the mark 64, it becomes possible to enable the inspector to notice the presence of the lesion 46, and to thereby prevent overlooking of the lesion 46. However, if the display of the mark 64 is continued for a period longer than necessary, the mark 64 may become an obstacle in observing the lesion 46 and the peripheral tissues thereof. In consideration of this, in the present embodiment, a function is provided to the indication controller, to forcibly restrict the mark display.

Figure 3:
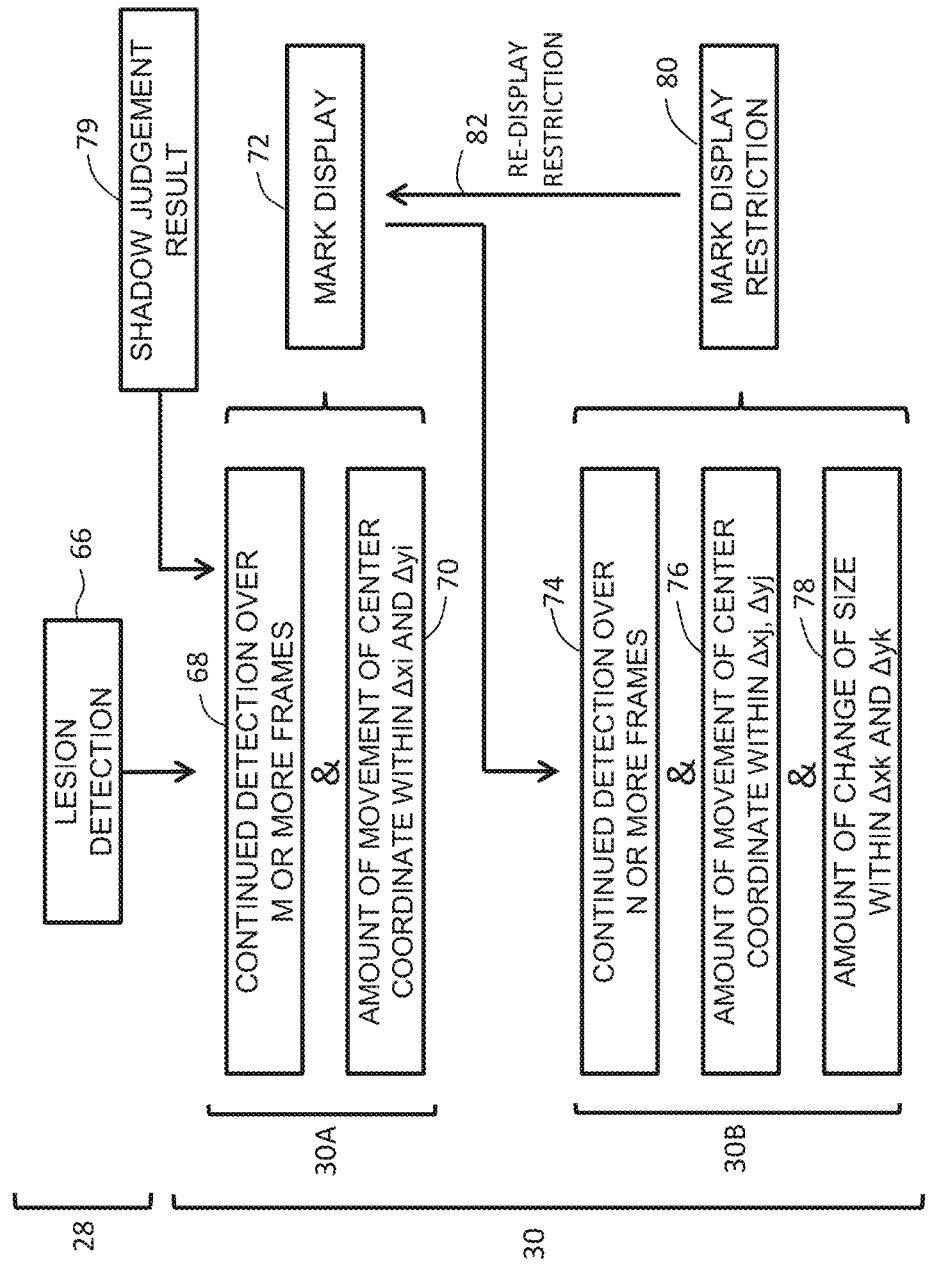
FIG. 3 is a diagram for explaining a mark display condition and a mark display restriction condition.

FIG. 3 shows examples of the mark display condition and the mark display restriction condition. As described above, lesion detection 66 is executed by the image analyzer 28. The indication controller 30 executes mark display control 30A and mark display restriction control 30B. More specifically, in the illustrated example configuration, the mark display condition includes a first condition 68 and a second condition 70, and it is judged that the mark display condition is satisfied when both of these conditions are satisfied. The first condition 68 is a condition determining that the lesion is continued to be detected over m or more frames. Here, m is an integer greater than or equal to 2, and is, for example, 3. The second condition 70 is a condition determining that an amount of movement of a center coordinate between a reference frame and a current frame is within a certain range. In the illustrated example configuration, as the certain range, a range $\Delta xi$ in the horizontal direction and a range $\Delta yi$ in the vertical direction are defined. The reference frame is, for example, a frame in which the lesion is first detected. Alternatively, a frame one frame previous to this frame may be set as the reference frame. When both the first condition 68 and the second condition 70 are simultaneously satisfied, a mark display 72 is decided, and the mark surrounding the lesion is displayed in a form overlapping the tomographic image. Prior to application of mark display restriction to be described below, display of the mark is continued so long as detection of the lesion is continued.

In judging whether or not the mark display condition is satisfied, a shadow judgment result 79 may be taken into consideration. Here, a shadow is caused due to a partial floating of the probe transmission/reception surface from the body surface, or the like. The shadow is typically a phenomenon in which, on the tomographic image, a partial section in the horizontal direction is displayed in a black band form over an entire region in the vertical direction. For example, the shadow may be caused due to an end of the transmission/reception surface moving away from the surface of the living body, or due to contact of the transmission/reception surface with a nipple. The presence or absence of the shadow, and a range of the shadow may be identified, for example, by identifying a valley portion in a profile formed by projecting the tomographic image on the horizontal axis. For example, when the shadow is caused and the detection of the lesion is stopped for a certain period due to the shadow, it is still regarded that detection of the lesion is continued.

In the illustrated example configuration, the mark display restriction condition includes a first condition 74, a second condition 76, and a third condition 78. When all three of these conditions are simultaneously satisfied, mark display restriction 80 is decided, and the mark is deleted from the screen even if detection of the lesion is continued. In the present embodiment, after the mark display restriction is started, even when the detection of the lesion is stopped, if the period of stopped detection is within a certain period (for example, 1 second or 2 seconds), re-display of the mark is restricted (refer to reference numeral 82).

More specifically, in the illustrated example configuration, the first condition 74 is a condition determining that detection of the lesion is continued over n frames. Here, n is an integer greater than or equal to m, and is, for example, 30 or 60. The number n may be designated by the user. Alternatively, the number n may be set automatically according to the circumstances.

The second condition 76 is a condition determining that the amount of movement of the center point between the reference frame and the current frame is within a first range. The first range is more specifically $\Delta xj$ in the horizontal direction and $\Delta yj$ in the vertical direction. The first range may be designated by the user, or may be set automatically according to the circumstances.

The third condition 78 is a condition determining that the amount of change of the size between the reference frame and the current frame is within a second range. The second range is more specifically $\Delta xk$ in the horizontal direction and $\Delta yk$ in the vertical direction. The second range may be designated by the user, or may be set automatically according to the circumstances.

In the second condition 76 and the third condition 78, the reference frame is, for example, a frame in which the lesion is first detected when detection of the lesion is continued. Alternatively, a previous frame of this frame may be set as the reference frame, or a frame in which the mark display is started may be set as the reference frame. Alternatively, another frame may be set as the reference frame.

When all of the first condition 74 through the third condition 78 are simultaneously satisfied, it is highly likely that display of a same lesion is continued and that the inspector recognizes the lesion. Thus, the mark display restriction 80 is decided, and the mark is deleted from the screen.

Figure 4:
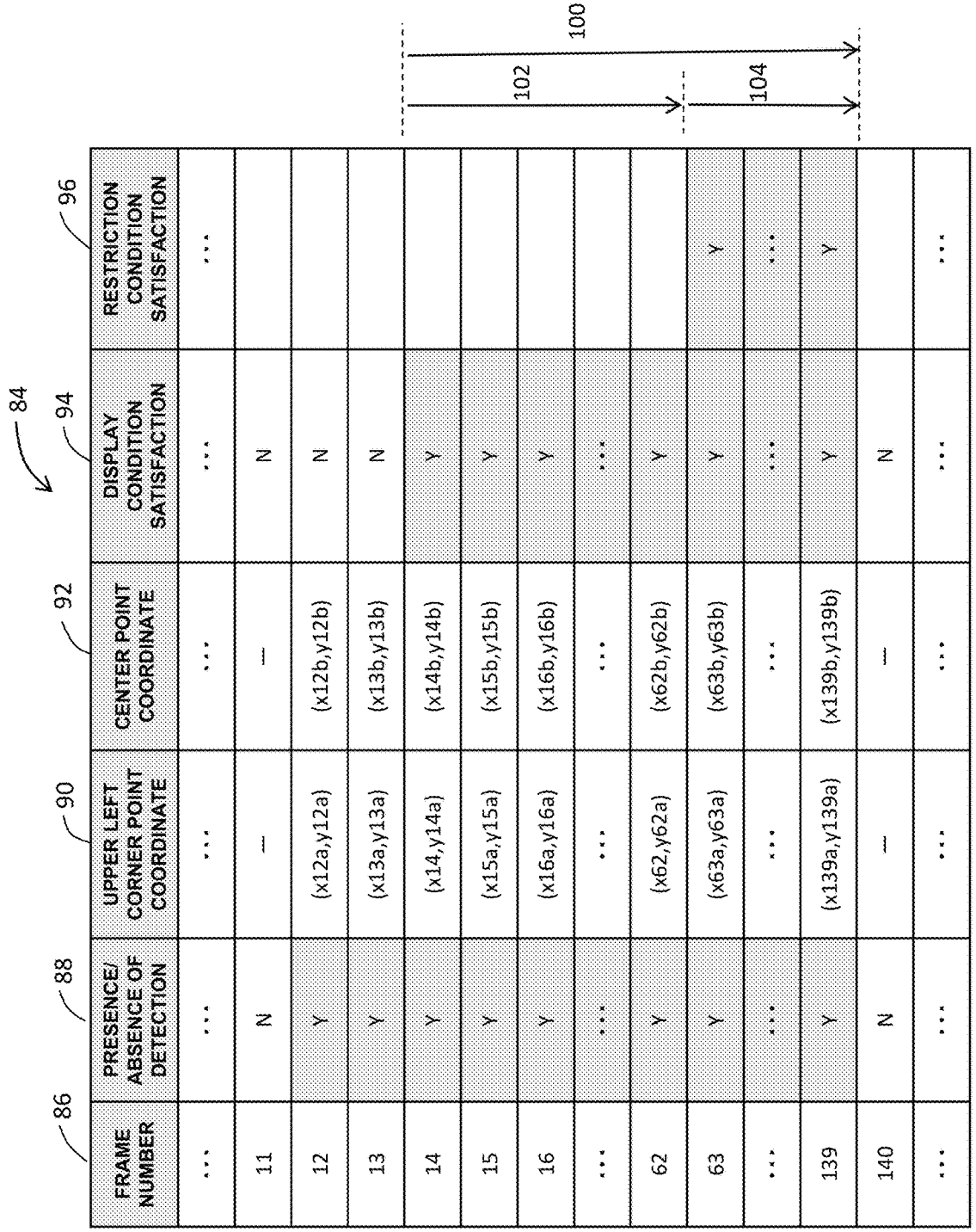
FIG. 4 is a diagram showing lesion information and control based thereon.

A table 84 shown in FIG. 4 includes a transition of the lesion information. The table 84 is formed from a plurality of records. Each individual record includes a frame number 86, a lesion detection flag (Y) 88, a coordinate 90 of the upper left corner point, a coordinate 92 of the center point, a flag (Y) 94 showing satisfaction of the mark display condition, and a flag (Y) 96 showing satisfaction of the mark display restriction condition. Slightly after the start of the lesion detection, the mark display is started. Reference numeral 100 shows a period in which detection of the lesion is continued. Reference numeral 102 shows a mark display period. After some time has elapsed after the mark display is started, the mark display restriction condition is satisfied, and the mark display is forcibly restricted in a period shown by reference numeral 104. With this process, obstruction, by the mark, of the observation of the lesion and the peripheral tissues is prevented.

Figure 5:
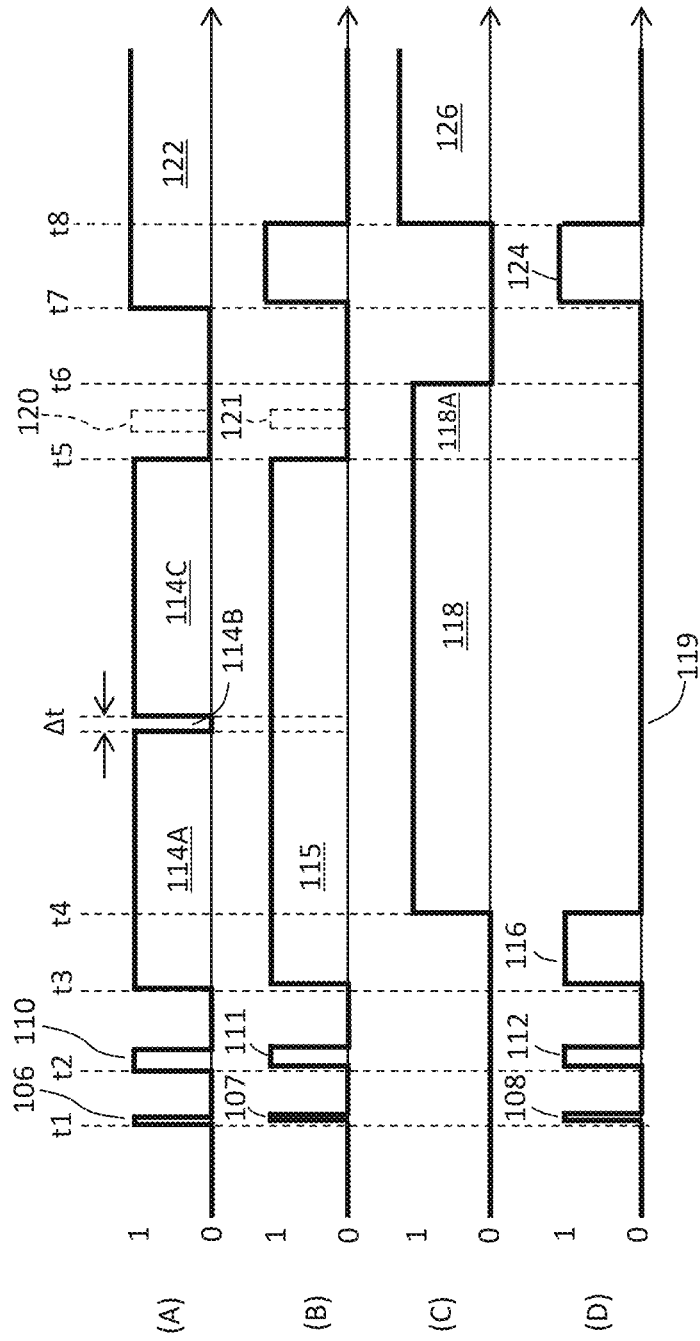
FIG. 5 is a timing chart showing an example operation.

In FIG. 5, (A) shows a lesion detection flag. In the flag, 0 indicates non-detection, and 1 indicates detection (corresponding to Y described above). In addition, (B) indicates whether or not the mark display condition is satisfied, with 0 indicating non-satisfaction and 1 indicating satisfaction (corresponding to Y described above). Further, (C) indicates whether or not the mark display restriction condition is satisfied, with 0 indicating non-satisfaction and 1 indicating satisfaction (corresponding to Y described above). Moreover, (D) indicates presence or absence of an actual mark display, with 0 indicating non-display and 1 indicating display. When the mark display condition shown in (B) is satisfied, and the mark display restriction condition shown in (C) is not satisfied, the mark is displayed.

A specific process will now be described. At a timing t1, detection of the lesion is started, and the detection is continued only for a short period of time (refer to reference numeral 106). Slightly after the timing t1, the mark display condition is satisfied (refer to reference numeral 107), and the mark is displayed only for a short period of time (refer to reference numeral 108). At a timing t2, the lesion is again detected, and the detection is also continued only for a relatively short period of time (refer to reference numeral 110). With this process, the mark display condition is satisfied for a short period of time (refer to reference numeral 111), and the mark is displayed based on this satisfaction, for a short period of time (refer to reference numeral 112). At a timing t3, detection of the lesion is again started, and the detection is continued for a relatively long period (refer to reference numerals 114A and 114C). However, during a period $\Delta t$ within this period, a shadow is instantaneously caused, and the detection of the lesion is temporarily stopped (refer to reference numeral 114B). Even with the temporary stopping of the detection, the satisfaction of the mark display condition is maintained for a certain period (refer to reference numeral 115).

Slightly after the timing t3, the mark display is re-started, but at a timing t4, the mark display restriction condition is satisfied, and the mark is deleted at the timing t4 (refer to reference numeral 116). The mark display restriction condition is continued to be satisfied for a certain period (refer to reference numeral 118).

At a timing t5, the lesion is non-detected, but in the present embodiment, the mark display restriction state is continued for a certain period from the timing t5. If the lesion is again detected during an extension period 118A (refer to reference numerals 120 and 121), the mark is not displayed. This is because, for a same lesion, the necessity for again displaying a mark is low. Further, if the mark is again displayed when detection of the lesion is accidentally stopped, the mark may become obstructive. Alternatively, a configuration may be employed in which such a mark re-display restriction; that is, the extension period 118A, is not provided. Alternatively, the re-display of the mark may be restricted while it is possible to reliably confirm that the lesion is the same lesion. Desirably, the mark display condition and the mark display restriction condition are adaptively determined in consideration of needs of and operability by the user.

At a timing t7, the lesion is again detected, and then, the detected state is continued (refer to reference numeral 122). With this process, the mark display condition is satisfied, and the mark is again displayed (refer to reference numeral 124). From a timing t8 and on, the mark display restriction condition is satisfied (refer to reference numeral 126), and the mark is again forcibly deleted after the timing t8.

In the present embodiment, separate judgments are made in the horizontal direction and the vertical direction, but alternatively, the judgments may be integrated. For example, a configuration may be employed in which it is judged that the lesion is the same lesion based on a movement distance of the center point.

In the following, alternative configurations will be described.

Figure 6:
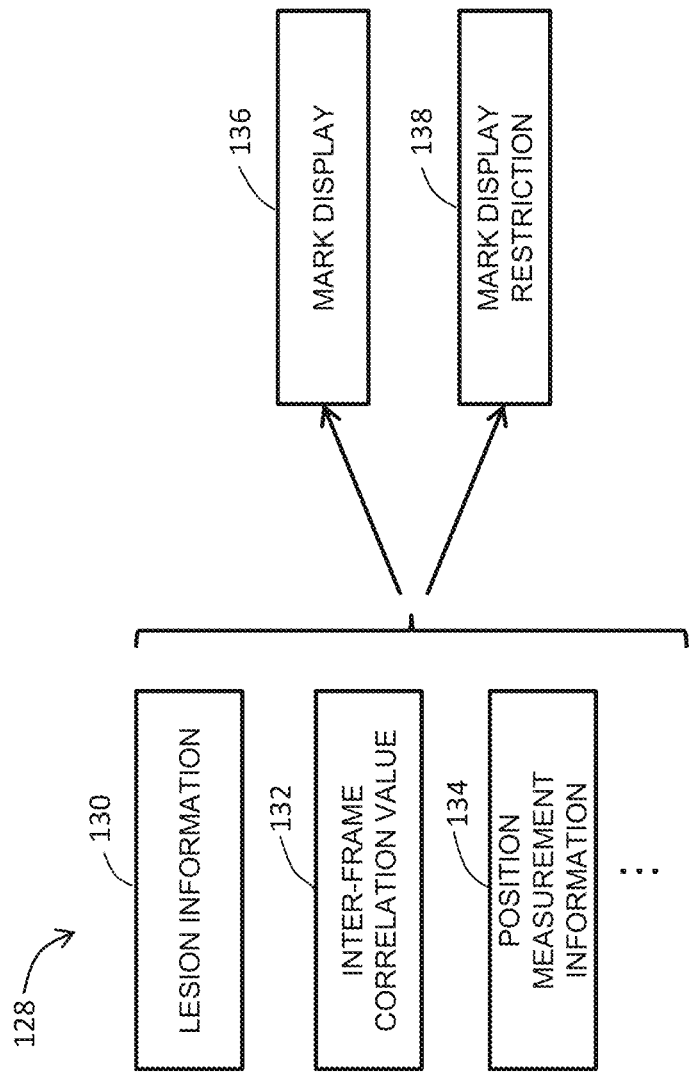
FIG. 6 is a diagram showing other examples of the mark display condition and the mark display restriction condition.

As shown in FIG. 6, mark display 136 and mark display restriction 138 may be decided based on a set of information 128. In the illustrated example configuration, the set of information 128 includes lesion information 130, an inter-frame correlation value 132, position measurement information 134, or the like. The lesion information 130 includes various information such as a lesion detection flag, movement information of the center point of the lesion, and information of change of size of the lesion. The inter-frame correlation value 132 is a correlation value calculated between individual frames. When an amount of movement of the probe is small, a difference of brightness information between the frames is low. The position measurement information 134 is information measured by a position measurement device, and is information showing a movement of the probe. According to the structure of FIG. 6, it is possible to adequately judge whether or not a mark is to be displayed, and whether or not a displayed mark is to be deleted, based on contents of the ultrasonic image and the movement of the probe.

Figure 7:
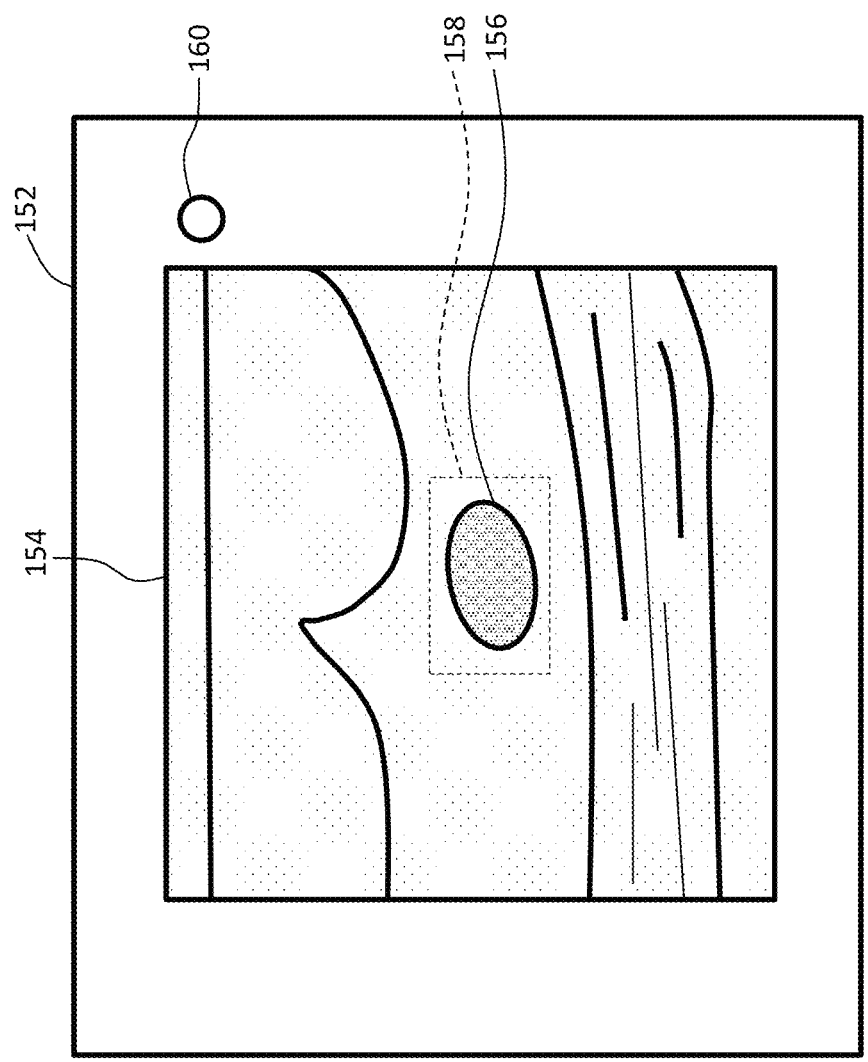
FIG. 7 is a diagram showing another mark displayed in the mark display restriction state.

FIG. 7 shows a tomographic image 154 displayed on a screen 152 of the display. The tomographic image 154 includes a lesion 156. The illustrated state is a state in which a mark 158 is deleted. In place of the display of the mark 158, a mark 160 is shown at an outer side (margin region) of the tomographic image 154. The mark 160 is a display element showing a state in which the lesion is being detected. Even when the mark 158 is deleted, through the display of the mark 160, it is possible to recognize that the lesion 156 in the tomographic image 154 is being automatically detected.

Figure 8:
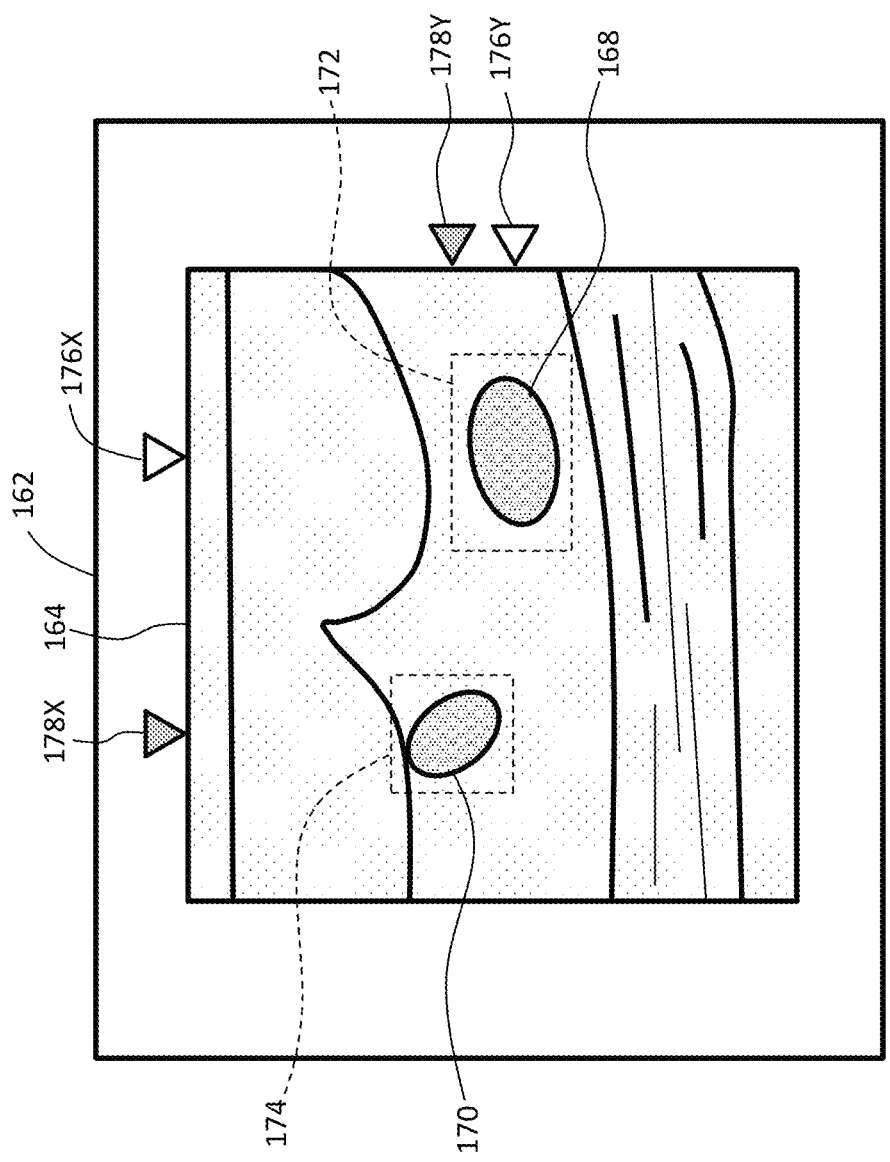
FIG. 8 is a diagram showing a plurality of mark sets.

FIG. 8 shows a tomographic image 164 displayed on the screen of the display. The tomographic image 164 includes a first lesion 168 and a second lesion 170. A mark 172 indicating the first lesion 168 is deleted, and a mark 174 indicating the second lesion 170 is also deleted. In place of the mark 172, marks 176X and 176Y forming a first mark set are displayed at an outer side (margin region) of the tomographic image 164. Similarly, in place of the mark 174, marks 178X and 178Y forming a second mark set are displayed at the outer side of the tomographic image 164.

The mark 176X shows an X coordinate of the center point of the first lesion 168, and is displayed at an X coordinate identical to the X coordinate of the center point. The mark 176Y shows a Y coordinate of the center point of the first lesion 168, and is displayed at a Y coordinate identical to the Y coordinate of the center point. The mark 178X shows an X coordinate of the center point of the second lesion 170, and is displayed at an X coordinate identical to the X coordinate of the center point. The mark 178Y shows a Y coordinate of the center point of the second lesion 170, and is displayed at a Y coordinate identical to the Y coordinate of the center point. The first mark set is displayed with a first color, and the second mark set is displayed with a second color different from the first color. With the structure of FIG. 8, even after the display of a plurality of marks surrounding a plurality of lesions disappears, the positions of the plurality of lesions can be easily identified.

Figure 9:
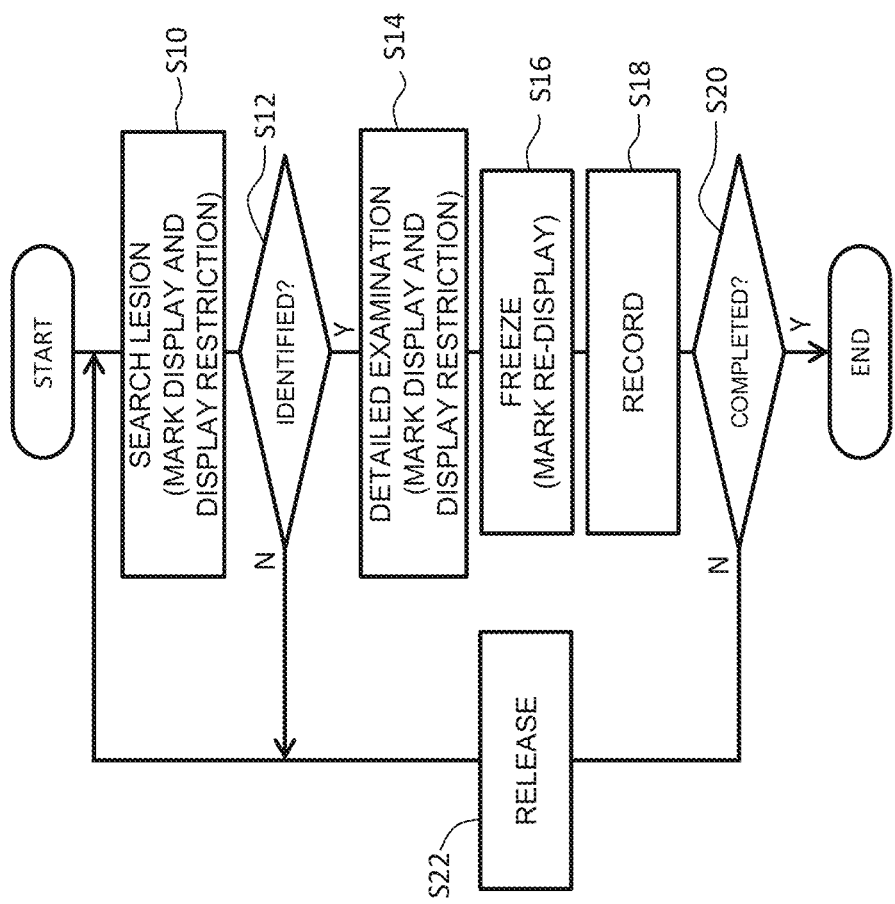
FIG. 9 is a flowchart showing an example operation.

FIG. 9 shows an example operation. The example operation includes a probe operation by the inspector. In S10, a lesion is searched by a manual scanning of the probe over a surface of the body. During this process, when the mark display condition is satisfied, the mark is displayed, and then, when the mark display restriction condition is satisfied, the display of the mark is forcibly restricted. When the lesion is identified; that is, when the inspector notices the lesion in S12, a position and an orientation of the probe are adjusted in S14, and the lesion is examined in more detail. In this case, when the mark display restriction condition is satisfied, the mark disappears. With this configuration, the obstruction by the mark in the observation of the lesion and the peripheral tissues can be prevented.

In S16, a freeze operation is performed. With this process, the transmission and reception are temporarily stopped, and the video image is switched to a stationary image. When the displayed image is an image on which the mark display restriction is applied, the mark is again displayed. In other words, the mark surrounding the lesion appears on the screen. Then, in S18, the displayed image (image including the mark) is recorded in a storage unit. The image becomes a part of an examination report.

In the frozen state, when a group of images acquired in the past are to be sequentially displayed, the mark is displayed for the images for which the mark display restriction is applied. During the recording of the image, both an image with a mark and an image without a mark may be recorded. Alternatively, a graphic image including the mark and the tomographic image may be separately recorded.

When a completion of the present process is not judged in S20, in S22, the freeze is released, and the processes from S10 and on are again executed. The example operation of FIG. 9 is merely exemplary, and various other example operations may be employed.

In a case in which the tomographic image is displayed in real time while the probe operation is executed, by applying the mark display control and the mark display restriction control described above, the ultrasonic examination time can be shortened. Alternatively, a frame data array may be transferred from the ultrasound diagnostic apparatus to an information processor such as a computer, and the information processor may cause display of a tomographic image which is a video image. In this case, the mark display and the mark display restriction described above may be applied. Alternatively, an image other than the tomographic image may be displayed as the ultrasonic image.

The invention claimed is:

1. An ultrasound diagnostic apparatus comprising:
at least one processor which when executing a program configures the processor to:
detect a lesion included in an ultrasonic image which is a real-time video image, and that outputs lesion information when the lesion is detected; and
cause a mark for indicating the lesion to be displayed on the ultrasonic image based on the lesion information, and restrict display of the mark when a mark display restriction condition is satisfied by a continued detection of the lesion;
delete the mark from the ultrasonic image when the mark display restriction condition is satisfied even if the lesion continues to be detected; and
judge that the mark display restriction condition is satisfied, based on the lesion information,
wherein the lesion information includes position information which shows a position of the lesion, and size information which shows a size of the lesion,
wherein the at least one processor is further configured to judge that the mark display restriction condition is satisfied, based on at least one of the position information and the size information of the lesion, and
wherein the mark display restriction condition includes a first condition, a second condition, and a third condition, the first condition being a condition of determining that detection of the lesion is continued over n frames, where n is an integer greater than or equal to m, the second condition is a condition of determining that the amount of movement of a center coordinate of the lesion between the reference frame and the current frame is within a second range, the third condition being a condition of determining that the amount of change of the size of the lesion between the reference frame and the current frame is within a third range, and when all of the first, second and third conditions are simultaneously satisfied, the mark is not displayed on the screen.

2. The ultrasound diagnostic apparatus according to claim 1, wherein
when a freeze operation is performed in a state in which the display of the mark is restricted, the at least one processor is further configured to again display the mark on the ultrasonic image which is frozen.

3. The ultrasound diagnostic apparatus according to claim 1, wherein
the mark has a form surrounding the lesion, and
in a state in which the display of the mark is restricted, the at least one processor is further configured to cause display of another mark, for indicating detection of the lesion, at an outer side of the ultrasonic image.

4. A method of assisting diagnosis, the method comprising:
detecting a lesion included in an ultrasonic image;
displaying a mark which surrounds the lesion on the ultrasonic image based on lesion information which is produced when the lesion is detected;
restricting display of the mark when a mark display restriction condition is satisfied by a continued detection of the lesion;
deleting the mark from the ultrasonic image when the mark display restriction condition is satisfied even if the lesion continues to be detected; and
judging that the mark display restriction condition is satisfied, based on the lesion information,
wherein the lesion information includes position information which shows a position of the lesion, and size information which shows a size of the lesion,
wherein the at least one processor is further configured to judge that the mark display restriction condition is satisfied, based on at least one of the position information and the size information of the lesion, and
wherein the mark display restriction condition includes a first condition, a second condition, and a third condition, the first condition being a condition of determining that detection of the lesion is continued over n frames, where n is an integer greater than or equal to m, the second condition is a condition of determining that the amount of movement of a center coordinate of the lesion between the reference frame and the current frame is within a second range, the third condition being a condition of determining that the amount of change of the size of the lesion between the reference frame and the current frame is within a third range, and when all of the first, second and third conditions are simultaneously satisfied, the mark is not displayed on the screen.

5. A non-transitory computer-readable storage medium which stores program executed by at least one processor to cause the processor to perform functions of:
displaying a mark which surrounds a lesion on an ultrasonic image, based on lesion information which is produced when the lesion included in the ultrasonic image is detected;
restricting display of the mark when a mark display restriction condition is satisfied by a continued detection of the lesion;
deleting the mark from the ultrasonic image when the mark display restriction condition is satisfied even if the lesion continues to be detected; and
judging that the mark display restriction condition is satisfied, based on the lesion information,
wherein the lesion information includes position information which shows a position of the lesion, and size information which shows a size of the lesion,
wherein the at least one processor is further configured to judge that the mark display restriction condition is satisfied, based on at least one of the position information and the size information of the lesion, and
wherein the mark display restriction condition includes a first condition, a second condition, and a third condition, the first condition being a condition of determining that detection of the lesion is continued over n frames, where n is an integer greater than or equal to m, the second condition is a condition of determining that the amount of movement of a center coordinate of the lesion between the reference frame and the current frame is within a second range, the third condition being a condition of determining that the amount of change of the size of the lesion between the reference frame and the current frame is within a third range, and when all of the first, second and third conditions are simultaneously satisfied, the mark is not displayed on the screen.

6. An ultrasound diagnostic apparatus comprising:
at least one processor which when executing a program configures the processor to:
detect a lesion included in an ultrasonic image which is a real-time video image, and that outputs lesion information when the lesion is detected; and
cause a mark for indicating the lesion to be displayed on the ultrasonic image based on the lesion information, and restrict display of the mark when a mark display restriction condition is satisfied by a continued detection of the lesion; and
judge that the mark display restriction condition is satisfied, based on the lesion information,
wherein the lesion information includes position information which shows a position of the lesion, and size information which shows a size of the lesion,
wherein the at least one processor is further configured to judge that the mark display restriction condition is satisfied, based on at least one of the position information and the size information of the lesion,
wherein a mark display condition includes a first condition and a second condition, the first condition being a condition of determining that the lesion is continued to be detected over m or more frames, where m is an integer greater than or equal to 2, the second condition being is a condition of determining that an amount of movement of a center coordinate of the lesion between a reference frame and a current frame is within a first range, and the mark can be displayed when both of the first and second conditions have been met, and
wherein the mark display restriction condition includes a third condition, a fourth condition, and a fifth condition, the third condition being a condition of determining that detection of the lesion is continued over n frames, where n is an integer greater than or equal to m, the fourth condition is a condition of determining that the amount of movement of the center coordinate of the lesion between the reference frame and the current frame is within a second range, the fifth condition being a condition of determining that the amount of change of the size of the lesion between the reference frame and the current frame is within a third range, and when all of the third, fourth and fifth conditions are simultaneously satisfied, the mark is not displayed on the screen.

7. An ultrasound diagnostic apparatus comprising:
at least one processor which when executing a program configures the processor to:
detect a lesion included in an ultrasonic image which is a real-time video image, and that outputs lesion information when the lesion is detected; and
cause a mark for indicating the lesion to be displayed on the ultrasonic image based on the lesion information, and restrict display of the mark when a mark display restriction condition is satisfied by a continued detection of the lesion; and
judge that the mark display restriction condition is satisfied, based on the lesion information,
wherein the lesion information includes position information which shows a position of the lesion, and size information which shows a size of the lesion, wherein the at least one processor is further configured to judge that the mark display restriction condition is satisfied, based on at least one of the position information and the size information of the lesion, wherein the mark display restriction condition includes a first condition, a second condition, and a third condition, the first condition being a condition of determining that detection of the lesion is continued over n frames, where n is an integer greater than or equal to m, the second condition is a condition of determining that the amount of movement of a center coordinate of the lesion between the reference frame and the current frame is within a second range, the third condition being a condition of determining that the amount of change of the size of the lesion between the reference frame and the current frame is within a third range, and when all of the first, second and third conditions are simultaneously satisfied, the mark is not displayed on the screen.

\* \* \* \* \*